United States Patent [19]

Von Albertini

[11] Patent Number: 4,670,008
[45] Date of Patent: Jun. 2, 1987

[54] HIGH FLUX THREADED NEEDLE

[76] Inventor: Beat Von Albertini, 617 Linden Dr., Beverly Hills, Calif. 90210

[21] Appl. No.: 750,892

[22] Filed: Jul. 1, 1985

[51] Int. Cl.$^4$ ............................................. A61M 5/00
[52] U.S. Cl. .................................... 604/165; 604/172
[58] Field of Search .............. 604/165, 164, 168, 179, 604/188, 264, 272, 273, 280, 239

[56] References Cited

U.S. PATENT DOCUMENTS

| 1,248,492 | 12/1917 | Hill | 604/165 |
| 1,888,349 | 11/1932 | Jacoby | 604/263 |
| 3,727,613 | 4/1973 | Sorenson et al. | 604/168 X |
| 4,013,080 | 3/1977 | Froning | 604/165 |
| 4,215,690 | 8/1980 | Oreopoulos et al. | 604/272 X |

FOREIGN PATENT DOCUMENTS

| 1541237 | 7/1973 | Fed. Rep. of Germany | 604/272 |
| 2466994 | 5/1981 | France | 604/272 |

Primary Examiner—Stephen C. Pellegrino
Attorney, Agent, or Firm—Blakely, Sokoloff, Taylor & Zafman

[57] ABSTRACT

The present invention is a needle for injecting or removing liquid from a body comprising a trocar have a sharpened end disposed within a generally conically shaped cannula with the trocar sharpened end extending past the end of the cannula. The cannula may have threads on its end to facilitate insertion. The trocar is removable from the cannula.

20 Claims, 4 Drawing Figures

HIGH FLUX THREADED NEEDLE

FIELD OF THE INVENTION

This invention relates to cannulas and hypodermic needles, and more particularly, to a hypodermic needle having a threaded portion to secure said needle in a body and an enlarged internal diameter for optimized flow rate of liquids passing therethrough.

BACKGROUND OF THE INVENTION

Needles for application or insertion into an artery, vein or other blood vessel or cavity are utilized for the withdrawal of blood from a blood vessel, or body cavity, and/or the delivery of blood or other fluid to such blood vessel or body cavity. One common usage of such needles is in hemo-dialysis in which blood is removed from a patient, purified and returned to the patent. In dialysis and other medical procedures relating to the injection and/or withdrawal of fluids in the body, it is desirable and generally important to optimize the rate at which the blood or other liquid flows through the needle. The major limitation in the rate of blood flow is the size of the cross-sectional area of the needle, since the tubing used to carry the blood to the dialysis equipment is of significantly greater diameter than the needle. Generally, the larger the cross-sectional area of a needle is throughout its length, the greater the flow rate of the liquid therethrough. In fact, the rate of flow of a liquid through a needle is proportional to the radius (r) of the needle raised to the fourth power and inversely proportional to the length of the needle, according to the Hagen-Poiseuille's equation, set forth $$Q = (\pi r^4 \Delta P)/(8 \mu L)$$

Q=flow
r=radius of conduit
ΔP=pressure gradient
L=length of conduit
μ=constant

The pressure gradient (ΔP) that can safely be applied to the blood is limited by the capacity of the blood cells to withstand the pressure without hemolyzing (rupturing). High negative pressure results in damage to the cell membrane and hemolysis. Therefore, the only means to optimize flow through the needle is to modify the radius and the length of the needle. The length is difficult to modify because of certain inherent factors such as the distance of the target blood vessel to the surface of the skin and the best or preferred angle for inserting the needle into the blood vessel. Therefore, the best and most common parameter of the above equation which is modified to increase the fluid flow through a needle is the radius.

In the case of kidney dialysis, the criticality of the rate of blood flow for dialysis patients can be better understood when it is considered that each adult kidney patient requiring dialysis must receive dialysis treatment three times a week for his or her life, and each such treatment requires typically approximately four hours to complete. Thus, ignoring other factors, according to Poiseuille's equation, the doubling of the internal diameter of a needle throughout its length would result in a sixteen-fold increase in the rate of blood flow, which, in turn, would result in a sixteen-fold time reduction for each dialysis treatment. Accordingly, a reduction in treatment time, in turn, would reduce the cost of dialysis treatment substantially. Even a 10 percent increase in needle diameter results in approximately a 46 percent ($1.1^4$) increase in flow rate. Prior art dialysis needles have an internal diameter in the range of approximately 1.6 to 2.2 mm (generally, 16 gauge needles are used), which is generally larger than those used for hypodermic injections. Such needles are also generally manufactured with ultrathin wall thicknesses of 0.05 to 0.1 mm to obtain the smallest possible outer diameter with the greatest possible inner diameter.

Of course, there are inherent problems involved with using needles having particularly large cross-sectional diameters (e.g. large gauge needles). For example, large gauge needles tend to be more painful to a patient than smaller needles. Also, the larger puncture wound caused by a large gauge needle requires greater healing time. Further, larger gauge needles have a greater risk of infection as a result of the aforementioned larger hole and longer healing time. There is also a psychological factor involved, in that persons who are afraid of needles tend to have a greater fear of larger gauge needles.

Further, in this connection, it is also known that skin and blood vessels are flexible and elastic and can stretch to some degree when stretched at a reasonably slow rate. Needles used for dialysis, except for the beveled point used to cut a hole in the skin and blood vessel, are substantially of a uniform diameter throughout their length. Thus, prior art needles do not effectively rely on the ability of the skin and blood vessel to stretch to permit the insertion of a needle of relatively large diameter into a relatively small hole, but instead, cut a relatively large hole.

In addition, prior art needles, particularly those intended to remain in place for extended periods of time, have certain inherent problems with respect to their ability to remain fixed in place when inserted in the intended blood vessel or body cavity. In particular, such needles must be held in place by adhesive or other securing means; otherwise, the needle is easily displaced because the smooth sides thereof do not create enough resistance to be held in place.

The present invention overcomes the drawbacks of the prior art needles, providing a needle having a large internal diameter capable of being inserted into a blood vessel without puncturing a large hole in the skin and blood vessel or body cavity, which needle is securely disposed in a predetermined area.

SUMMARY OF THE INVENTION

The present invention comprises a needle for insertion into a blood vessel, body organ, body cavity and the like, having a pointed or sharpened puncturing member which creates a small hole in the skin, blood vessel or other internal tissue, thereby allowing a larger diameter threaded conical member to be threaded therein, thus stretching rather than cutting or tearing a hole in the patient. The inner diameter of the needle is enlarged even more when the puncturing member is removed, leaving only a short portion with relatively narrow diameter, the majority of the length of the needle having a substantially larger internal diameter than any prior art needle.

The invented needle comprises a hollow or solid trocar, said trocar having a sharpened point or bevel on one end thereof, and a conically shaped cannula disposed tightly around the trocar and removably attached thereto. The sharpened end of the trocar extends past the end of the cannula. The cannula is externally threaded near its end adjacent the trocar sharpened end so that it can be screwed into the skin and blood vessel, or other tissue without excessively enlarging the hole by insertion thereof. The end of the cannula is blunt and flexible to prevent damage to the tissue, vessel or organ in which it is placed, and to permit the cannula to bend in line with the vessel. The cannula may also include holes along its end to increase the fluid flow therein.

The trocar is removably attached to and preferably screwed into the cannula. If the trocar is hollow, a cap may be provided thereon to prevent leakage of blood therethrough after the needle is inserted into a blood vessel, until the trocar is removed from the cannula. With a hollow trocar, the ends of the cannula and trocar, respectively, opposite the sharpened end are preferably translucent or transparent so that when the device is properly inserted in its predetermined target area, such as a blood vessel, the user can observe blood flowing into the neck of the device to insure that the needle has been properly placed. This transparent region is preferably formed of flexible material so that it can be clamped to prevent fluid flow therethrough until the tubing or other receptacle is attached to the end of the needle.

In another embodiment of the present invention, the needle is conically shaped and hollow with a sharpened beveled end and threads on the exterior surface thereof. In this embodiment, there is no trocar, and the sharpened end of the cannula serves the same purpose. This embodiment has the advantages of having a larger diameter throughout the majority of its length so that an increased fluid flow capacity can be achieved relative to a standard, smooth, bare cylindrical needle. In addition, the threaded portion of the needle is held in place by the threads so that cumbersome procedures for securing the needle in place may be relaxed. Moreover, the threaded conical shape of the needle enables the user to puncture a small hole which can be stretched into a larger hole, rather than puncturing a larger hole to accommodate the large diameter of the conical needle.

In yet another embodiment, a needle having a substantially uniform cross-section through its length, with threads on the exterior surface thereof to facilitate insertion into the body is described. This embodiment can be provided with or without a trocar. Of course, if no trocar is provided, the end of the device comprises a sharpened beveled end for insertion directly into the body.

In use, to insert the invented needle into a blood vessel, body organ, body cavity, or the like, or a human or animal patient, first, the tip of the trocar is inserted up to the external threads on the cannula. The user can detect when the trocar tip is inserted into the blood vessel by observing the flow of blood into the needle through the transparent portion thereof.

In the second step the cannula is screwed into the blood vessel, body cavity or organ, or the like, over the trocar. In this manner, the skin and blood vessel surrounding the needle are stretched, rather than torn or cut by the cannula having a larger outer diameter than the trocar. Simultaneously with the threading of the cannula into the intended location, the trocar is removed therefrom so that it does not puncture a hole in the side of the blood vessel opposite the point of entry. In the preferred embodiment, the trocar is screwed out of the cannula as the cannula is screwed into the blood vessel. In this way an internal diameter of the cannula, which is greater than that of the trocar, is freely exposed.

The larger internal cross-sectional area of the cannula allows the blood or other fluid to flow at a faster rate than smaller conventional hypodermic or dialysis needles. Moreover, the hole actually cut by the invented needle is the same size or smaller than that of the prior art needles. When the dialysis or other treatment is completed, the cannula can be screwed out, and the skin and blood vessel around the hole are permitted to relax thereby partially closing up the hole.

DETAILED DESCRIPTION

The invented needle can be used for dialysis, blood transfusions, blood donations, intravenous feeding, femoral artery and vein catheterization, peritoneal dialysis, and any other medical intravenous or other fluid transfer applications in which the rate of liquid flow into or out of the body of a patient should be optimized.

Figure 1:
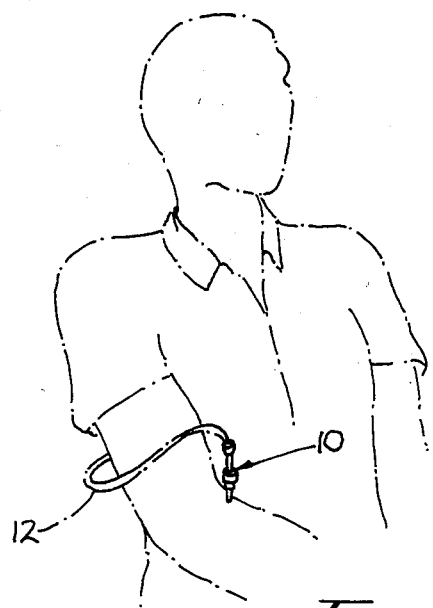
FIG. 1 shows a patient with the invented needle disposed in his arm.

In FIG. 1, a patient is shown with the invented needle 10 inserted into his arm and a tube 12 for providing liquid communication to a liquid source or receptacle, such as dialysis equipment, IV supply bottles, a blood or fluid collection receptacle and the like, which may be attached to the tube 12.

As described herein, the present invention can be used for any of the above-identified purposes. Although the following description generally refers to its use in connection with withdrawal of blood from a blood vessel, it will be obvious to one skilled in the art that the present invention can be applied in any medical applications environment to obtain the desired results.

Figure 2:
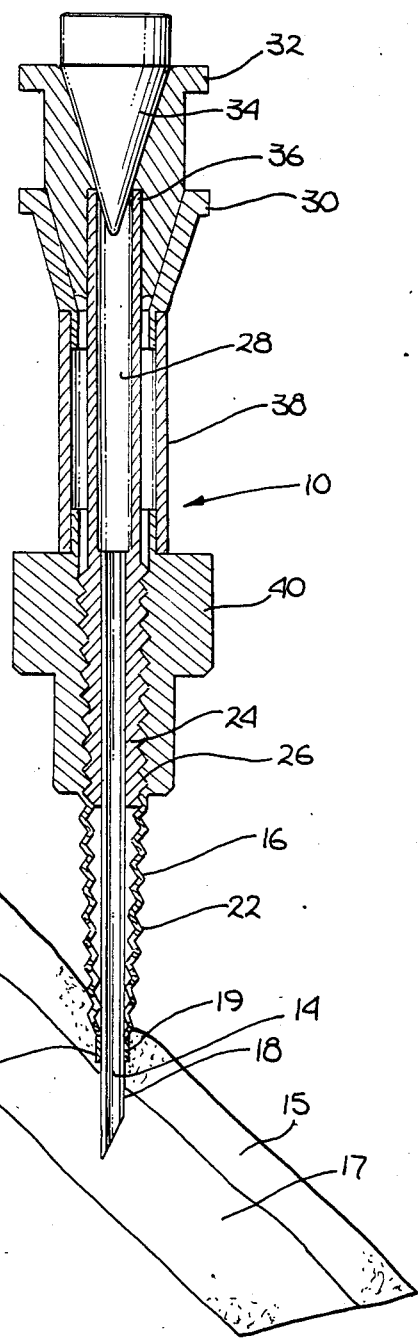
FIG. 2 is a cross-sectional side view of the invented needle disposed in a blood vessel.

As shown in FIG. 2, one embodiment of the invented needle 10 is shown disposed through the skin 15 and into the interior of a blood vessel 17. The needle 10 has two primary components, namely, a trocar 14 and a cannula 16. The trocar 14 may be either hollow or solid and, as shown in FIG. 2, the trocar is similar to a hollow needle, such as a standard hypodermic needle. A pointed tip 18 of the trocar 14 extends below the end 20 of the cannula 16 a sufficient distance so that when the tip 18 is inserted into the blood vessel 17, only the unthreaded end 20 of the cannula 16 will have penetrated the skin 15.

With respect to the conical shape of the cannula 16, particularly with respect to the threads 22 thereon, it is important to note that the threads 22 should be equidistantly spaced apart, notwithstanding the changing diameter of the cannula 16. This spatial arrangement of the threads insures that the cannula can be evenly and fully screwed in without cross-threading. The end 20 of the cannula is preferably blunt to avoid injury to the blood vessel or other tissue in which the needle is inserted. Particularly with respect to blood vessels, there is a concern that if end 20 is not sufficiently blunt, it may injure or pass completely through the vessel causing a hematoma so that it cannot draw blood therefrom or otherwise deposit fluid into the blood stream.

The end 20 including the threads 22 of the cannula is preferably made of flexible material to further prevent injury to the blood vessel, and, in addition, to permit the cannula 16 to bend in the direction of the blood vessel. In this way, the cannula 16 can be inserted down stream or upstream in the blood vessel to perform a catherization, or simply to secure the cannula in the blood vessel. The threaded portion 22 can be shorter or longer then that depicted in the drawings, and can have portions which are conically shaped and/or cylindrical through its length, as required, to achieve the desired result. In addition, the cannula 16 may have apertures 21 therealong to increase the number of potential fluid pathways to decrease the resistance to flow. Without apertures 21, the only entry or exit point for fluid into the cannula 16 is through end 20 thereof. However, with apertures 21 disposed in cannula 16 along the portion thereof disposed in the blood vessel 17 or other fluid filled target area, the blood can flow through the apertures 21 thereby providing additional volume to permit blood flow therethrough.

The trocar 14 is attached to the cannula 16 by a coupling means which can reversibly couple and uncouple the trocar 14 from the cannula 16. In the preferred embodiment shown in FIG. 2, the middle portion of the trocar 14 comprises externally disposed threads 24 and the middle portion of the cannula 16 comprises internally disposed threads 26. The cannula threads 26 preferably mate tightly with the trocar threads 24, forming a substantially fluid tight seal so that there is no blood leakage past the threads.

Above the trocar threads 24 is a neck portion 28 extending up to the end 30 of the cannula 16. In the preferred embodiment, a gripping means 32 is attached to the end 36 of the trocar 14. In use, the gripping means 32 is used to facilitate gripping the trocar 14 to screw it out of the cannula 16. If the trocar is hollow, both the trocar neck portion 28 and the cannula neck 38 are preferably translucent or transparent so that the user can observe when blood or other fluid flows therein. In this way, when the user is inserting the needle in a blood vessel, blood will appear in the neck portion when the needle is properly inserted in the vessel. Preferably, the cannula neck portion 38 is flexible so that it can be clamped to prevent blood flow therethrough after the trocar 14 is removed from within the cannula 16.

Also in the preferred embodiment, if the trocar is hollow, a cap 34 is disposed over the end 36 thereof to prevent blood leakage therefrom before the tube 12 shown in FIG. 1 is attached to the proximal end 30 of the cannula 16.

The inside diameter of the cannula 16 at distal end 20 is approximately equal to the outside diameter of the trocar 14 and thus, the smallest interior diameter of the cannula 16 is substantially relatively larger than the internal diameter of the trocar 14 or other standard dialysis needle. However, as one skilled in the art will readily recognize, the present invention is not deemed to be limited in any way by the preferred diameter size ranges set forth herein.

The end 20 of the cannula 16 is relatively tightly sealed against the tip 18 of the trocar 14 so that the cannula can fit into the hole made by the trocar. In this configuration, minimal trauma is caused to the skin, tissue and blood vessels when the cannula is inserted therein. However, the cannula end 20 does not so tightly engage the trocar end 18 that the trocar 14 cannot be removed from cannula 16. In the preferred embodiment, the ridge 19 or step between the trocar 14 and cannula 16 is as small as possible so as to minimize the trauma caused by insertion of the cannula 16 through the skin 15 and blood vessel 17. The ridge 19 is smooth and flexible while the threaded portion 22 is increasingly stiff in comparison, to permit the cannula to be threaded into the blood vessel.

Figures 3, 4:
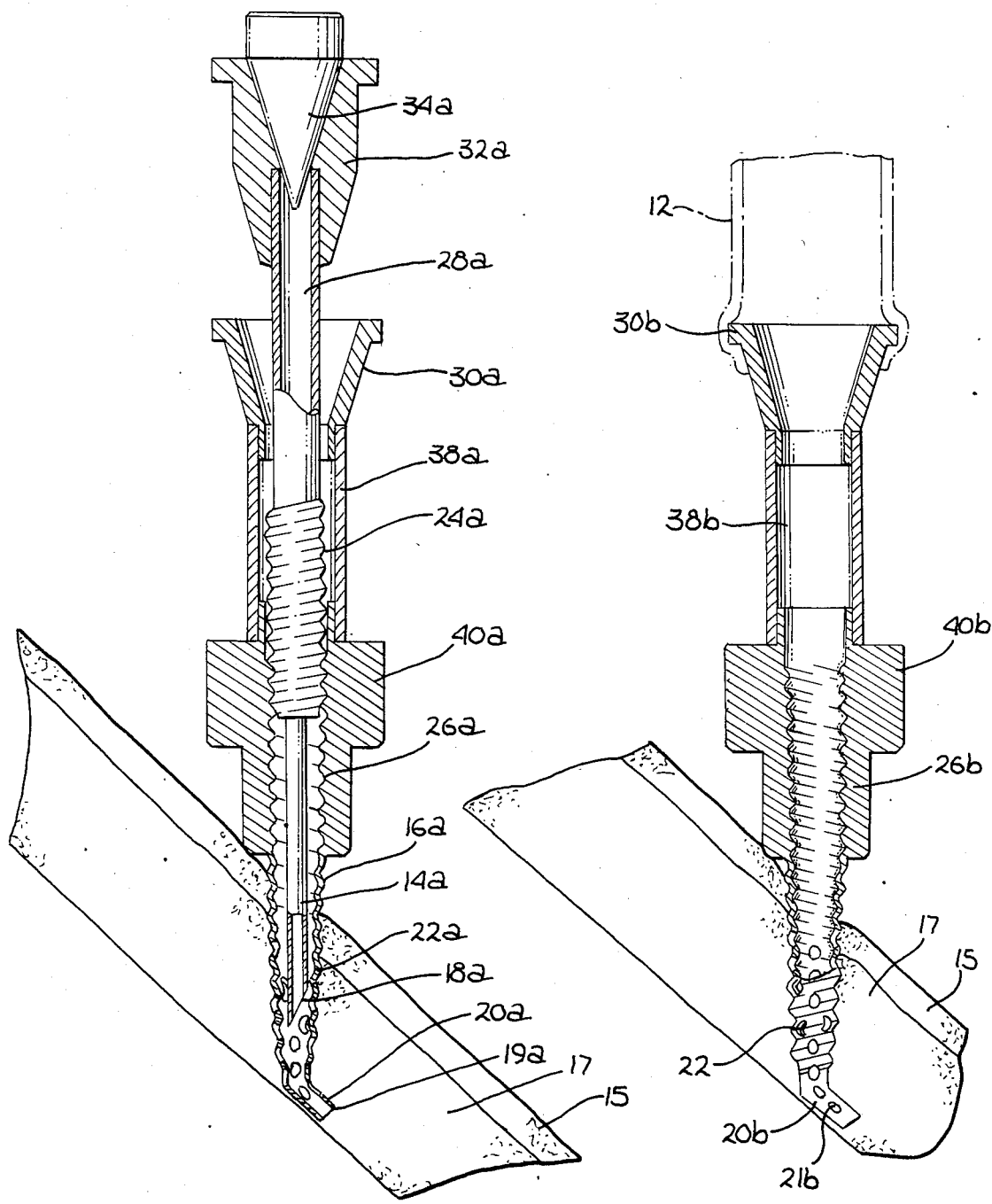
FIG. 3 illustrates the invented needle with the cannula fully disposed in the blood vessel and the trocar partially removed from the cannula.
FIG. 4 illustrates the invented needle with the trocar fully removed from the cannula.

The externally threaded portion 22 of the cannula 16 permits the cannula 16 to be threaded into the hole in the skin 15 and blood vessel 17 without having to enlarge the hole substantially. Once the needle 10 is inserted into the patient up to the end 20 of the cannula, the cannula is screwed into the skin 15 and the blood vessel 17, as shown in FIG. 3. A gripping means 40 is provided to hold and rotate the cannula 16 with respect to the trocar 14 and also with respect to the patient.

The upper portion of the cannula has a neck portion 38, above which is the end 30 which is preferably flared so that it can accommodate the trocar gripping means 32. The cannula neck portion 38 is also formed to securely hold tubes, catheters, syringes, and the like, to be attached to the needle 10. Preferably, a Luer-lock type of fastener is attached to permit fast, secure and standard attachment to syringes, tubing and the like.

In another embodiment, the invented needle has a beveled sharpened edge and a threaded portion thereabove, with the general shape of the needle being conical. However in this embodiment, a trocar is not provided. Instead, end 20 of the cannula is beveled and sharpened to cut through the skin and into the blood vessel or body cavity. This embodiment has the advantages over prior art needles of greater liquid flow rate because of the conical shape. Of course, it is not essential that the entire length of the needle be conically shaped, and it is contemplated that a portion of the length of said needle be cylindrically shaped. As described above, the threads permit easy, less painful insertion of the needle in the patient, allowing the skin and blood vessels to stretch rather than puncturing a lage hole therethrough. Moreover, the threads assist in securing the device in the patient by providing resistance to the needle being forced out. In order for the needle to be forced out, either the skin or other tissue through which the needle is disposed must be stretched over the thread, or the needle must rotate to thread itself out of the hold. This is in contrast to smooth wall cylindrical needles which need only slide directly out of the hole.

In yet another embodiment of the present invention, the needle is cylindrical and threaded. This embodiment has all the advantages of the threaded needle without the particular advantages of increased fluid flow rate.

In yet another embodiment of the present invention, the trocar is solid and pointed, and threaded along its exposed length. The cannula surrounds the trocar, and is also threaded, as described in the above first embodiment. This embodiment is contemplated as being particularly useful for peritoneal dialysis in which a cannula is disposed through the fascia, a very tough membrane overlying the peritoneal cavity, and fluid is pumped into the cavity and then removed therefrom. In this application, it is very difficult to force the cannula through the fascia, and great force must be applied thereto when using prior art needles. However, using this embodiment, the needle can be effectively and efficiently screwed into the fascia, without the effort of puncturing the same by direct pressure.

In operation, as shown in FIG. 2, the trocar 14 is inserted through the skin 15 and into the blood vessel 17 until the cannula threads 22 are adjacent the skin 15. At that point, the cannula 16 is rotated using the cannula grip means 40 thereby screwing the cannula 16 through the skin 15 and into the blood vessel 17. Simultaneously with rotaing the cannula 16, the trocar 14 is held stationary so that it is not inserted into the blood vessel any further than originally disposed in the initial insertion shown in FIG. 2. As shown in FIG. 3, trocar neck 28a is exposed outside the cannula end 30a. In this position, trocar tip 18a is approximately in the same position with respect to blood vessel 17a as trocar tip 18 is to blood vessel 17 in FIG. 2.

FIG. 3 illustrates the position of the elements of the invented needle 10 after the cannula 16a is fully inserted in the blood vessel 17a and the trocar 14a is partially retracted from the cannula 16a. The alphanumeric designation "a" in FIG. 3 indicates the position of each of the aforementioned elements after cannula 16a is inserted and trocar 14a is partially retracted. It should particularly be noted that although as shown in FIG. 3, the cannula external threads 22a are screwed into the skin 15a all the way so that ridge 46a of grip means 40a is adjacent the skin, in practice, the actual distance of insertion of the cannula depends on various medical considerations generally known in the art, such as the depth of the blood vessel beneath the skin and the desired angle of penetration.

FIG. 4 illustrates the invented needle 10b in use with the trocar (not shown) fully removed. The alphanumeric designation "b" in FIG. 4 indicates each of the aforementioned elements in position at this stage of operation of the present invention. The invention as shown allows for maximum blood flow therethrough. A full and completely clear channel has been created within cannula 16b, the narrowest portion thereof being the cannula tip 20b. The inside diameter of the cannula 16 is at least slightly larger than the outside diameter of the trocar 14. The present invention permits a much greater blood flow through the needle 10 than prior art needles, which are generally only the size of the trocar, or smaller and are cylindrically shaped, rather than conical. Moreover, the fact that the cannula is screwed into the skin and blood vessel rather than having it punched in allows the cannula to be of substantially larger diameter than a standard dialysis needle.

It is anticipated that blood flow in the range of 500 to 1,000 milliliters per minute can be obtained using the invented needle as compared with a flow rate of 200 to 300 milliliters per minute for a prior art dialysis needle. Accordingly, the time required for dialysis treatment of an adult is reduced from 4 hours per treatment using a prior art needle to approximately 1½ to 2 hours for a complete dialysis treatment using the present invention.

Also, as shown in FIG. 4, tube 12b is attached with a conical end (Luer-lock) to the end 32b or cannula 16b. When the medical procedure is terminated, the invented needle 10b is removed from the patient. To accomplish removal, the needle 10b is rotated, thereby screwing it out of the blood vessel 17b and skin 15b. Generally known medical procedures are then utilized to stop the bleeding.

It will be obvious to one skilled in the art that many modifications can be made to the present invention as described herein without departing from the nature and scope thereof. The sizes and relative distances presented are for illustration purposes and should not be construed to limit the scope of the invention. The steps in the operation of the present invention illustrate the preferred method of the inventor and are not, in any way, intended to limit the scope of the present invention.

I claim:

1. A needle for use in the removal of body fluids and the injection of liquids into the body, said needle being characterized by having a rapid liquid flow rate, comprising:

puncturing means for puncturing a hole in a body, said puncturing means having a point on one end thereof;

tube means substantially surrounding and removably attached to said puncturing means so that said point extends past the end of said tube means, said tube means having an increasing internal diameter from the end near said point to the end distant therefrom;

removal means for removing said puncturing means from said tube means through the end thereof distant from said point;

whereby said puncturing means is adapted to puncture a hole in a body, said tube means is adapted to be inserted in said hole following said puncturing means therein, said puncturing means being removably attached to said tube means such that when said puncturing means is removed from said body said tube means having an increasing internal diameter is provided for the rapid injection of fluids into the body or withdrawal of fluids therefrom.

2. A needle for use in the removal of body fluids and injection of liquids therein characterized by having a high volume liquid flow rate therethrough comprising:

a trocar having a first end comprising a sharpened point thereon and a middle portion and a second end comprising a gripping means;

a cannula disposed about said trocar, said cannula having:

a first end being positioned so that said sharpened point of said trocar extends beyond said first end of said cannula;

externally disposed threads near said first end for threading said cannula into body tissue thereby causing minimal tearing of said tissue; and a second end adjacent said trocar gripping means;

a coupling means for reversibly coupling said cannula to said trocar such that said trocar can be removed therefrom; and an internal diameter of increasing size from said first end to said second end;

whereby said trocar can be removed from said cannula after insertion of said cannula into a body thereby creating an enlarged pathway through said cannula for rapid fluid flow therethrough.

3. The needle of claim 2 wherein said coupling means comprises mating threaded portions on said cannula and said trocar whereby said trocar can be unscrewed from said cannula.

4. The needle of claim 2 wherein said cannula further comprises a connecting means on said second end for connecting said cannula tip a receptacle.

5. The needle of claim 2 wherein said cannula further comprises a connecting means on said second end for connecting said cannula to a receptacle.

6. The needle of claim 5 wherein said first end of said cannula further comprises apertures disposed therealong for providing fluid communication therethrough.

7. A needle for use in the removal of body fluids and injection of liquids therein characterized by having a high volume liquid flow rate therethrough comprising:
a trocar having a pointed first end, an externally threaded central portion and a gripping means on a second end; and
a cannula comprising:
   a first end and second end, said cannula being disposed about said trocar so that said point extends beyond said first end of said cannula;
   an externally threaded portion on said first end so that said first end can be threaded into a patient's skin and blood vessel with minimal trauma thereto;
   an internally threaded portion between said first and second ends adapted to mate with said externally threaded portion of said trocar whereby said trocar is removably attached to said second member by said internally threaded portion; and
   a gripping means to facilitate the threading of said cannula into and out of said skin and blood vessel;
   whereby said needle can be inserted into a blood vessel up to said sharpened point of said trocar, said cannula can be screwed into said blood vessel and said first member can be removed from said cannula thereby creating an enlarged conduit for the passage of fluid therethrough.

8. The needle of claim 7 wherein said trocar is hollow and comprising a beveled point on said first end.

9. The needle of claim 8 wherein said trocar further comprises a cap means thereon for preventing the flow of liquid through said trocar.

10. The needle of claim 7 wherein said trocar is solid.

11. The needle of claim 10 wherein said first end of said trocar is threaded along its length.

12. The needle of claim 7 wherein said cannula further comprises a connecting means on said second end for connecting said cannula to a receptacle.

13. The needle of claim 7 wherein said cannula externally disposed threads are adapted to be screwed into a blood vessel.

14. The needle of claim 8 wherein said trocar and said cannula furter comprise substantially transparent portions therealong so that fluid contained in said needle can be viewed therethrough.

15. The needle of claim 14 wherein said substantially transparent portion of said cannula is formed of flexible material so that said cannula can be clamped closed to prevent fluid flow therethrough.

16. The needle of claim 7 wherein said second member has an increasing internal diameter from said first end to said second end.

17. The needle of any of claims 1-6 or 7-15 wherein said internal diameter is generally conically shaped.

18. The needle any of claims 1-6 or 7-15 wherein said internal diameter is generally conically shaped.

19. A hypodermic needle conically shaped along at least one portion of its length comprising a sharpened beveled end, a threaded portion thereabove for threading said needle into a patient, an internal diameter of increasing size from said beveled end to the other end thereof, and an attachment means for attaching said needle to a receptacle or source.

20. The needle of any of claims 1-6, 7-17 or 16 wherein said internal diameter increases gradually and uniformly.

* * * * *

UNITED STATES PATENT AND TRADEMARK OFFICE
CERTIFICATE OF CORRECTION

PATENT NO. : 4,670,008
DATED : June 2, 1987
INVENTOR(S) : Von Albertini

It is certified that error appears in the above-identified patent and that said Letters Patent is hereby corrected as shown below:

| COLUMN | LINE | DESCRIPTION |
|---|---|---|
| [54] | | In the title between the words "FLUX" and "NEEDLE" please delete "THREADED" |
| [57] | | In the Abstract after the first paragraph please insert:<br><br>--In use, after the trocar punches a hole in the skin and blood vessel, the cannula is screwed therein. The trocar is then removed from inside the cannula to expose a large cross-section thereby permitting rapid flow of fluid through the cannula.<br><br>In another embodiment, the needle comprises a conically shaped cannula with a sharpened end and threads disposed around the outside thereof to facilitate insertion into a body.-- |
| 3 | 51 | Delete "or", second reference, and insert --of--. |
| 8 | 62 | Delete "tip a" and insert -- to a --. |

UNITED STATES PATENT AND TRADEMARK OFFICE
CERTIFICATE OF CORRECTION

PATENT NO. : 4,670,008
DATED : June 2, 1987
INVENTOR(S) : Von Albertini

It is certified that error appears in the above-identified patent and that said Letters Patent is hereby corrected as shown below:

Column 8, lines 63-65, delete Claim 5 and insert instead

-- 5. The needle of Claim 2 wherein said needle is adapted for use in dialysis. --

Signed and Sealed this

Second Day of February, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,670,008
DATED : June 2, 1987
INVENTOR(S) : Von Albertini

It is certified that error appears in the above-identified patent and that said Letters Patent is hereby corrected as shown below:

| COLUMN | LINE | |
|---|---|---|
| 10 | 22-23 | Please delete Claim 18 and insert in lieu thereof |
| | | --18. The needle of Claim 2 wherein said cannula is externally threaded near the end thereof adjacent said point.-- |

Signed and Sealed this

Twenty-first Day of June, 1988

*Attest:*

DONALD J. QUIGG

*Attesting Officer*     *Commissioner of Patents and Trademarks*